United States Patent [19]

Miskinyar

[11] Patent Number: 4,894,054

[45] Date of Patent: Jan. 16, 1990

[54] PRELOADED AUTOMATIC DISPOSABLE SYRINGE

[76] Inventor: Shir A. Miskinyar, 13342 Clinton St., Garden Grove, Calif. 92643

[21] Appl. No.: 208,486

[22] Filed: Jun. 20, 1988

[51] Int. Cl.[4] .............................................. A61M 5/20
[52] U.S. Cl. ..................... 604/136; 604/157
[58] Field of Search .................. 604/131, 135–139, 604/141, 143, 144, 156, 157

[56] References Cited

U.S. PATENT DOCUMENTS

| | | | |
|---|---|---|---|
| 2,605,765 | 8/1952 | Kollsman | 604/135 |
| 2,752,918 | 7/1956 | Uytenbogaart | 604/136 |
| 2,856,924 | 10/1958 | Rockwell et al. | 604/136 |
| 3,572,336 | 3/1971 | Hershberg | 604/136 |
| 3,702,609 | 11/1972 | Steiner | 604/139 |
| 3,712,301 | 1/1973 | Sarnoff | 604/136 |
| 4,227,528 | 10/1980 | Wardlaw | 604/139 |

FOREIGN PATENT DOCUMENTS 742024  9/1966  Canada .................. 604/138
2461272  7/1976  Fed. Rep. of Germany ...... 604/137

Primary Examiner—Dalton L. Truluck
Attorney, Agent, or Firm—Plante, Strauss, Vanderburgh

[57] ABSTRACT

There is disclosed a precharged disposable syringe consisting of a housing having a central aperture through which extends an actuator button to contact an internal piston mounted over a medication ampoule contained in the housing. The ampoule includes a dependent hypodermic needle and the ampoule is slightively mounted in the housing for movement between a recessed position where it is totally contained and supported within the housing and an extended position with the dependent needle projecting out of the housing. An actuator spring is located in the housing and is compressed and biased to move the piston and the ampoule into the projected position. Medication is discharged by the mechanically coupled actuator button and piston. The actuator button and piston is locked for safety with a dent and plastic ring.

22 Claims, 3 Drawing Sheets

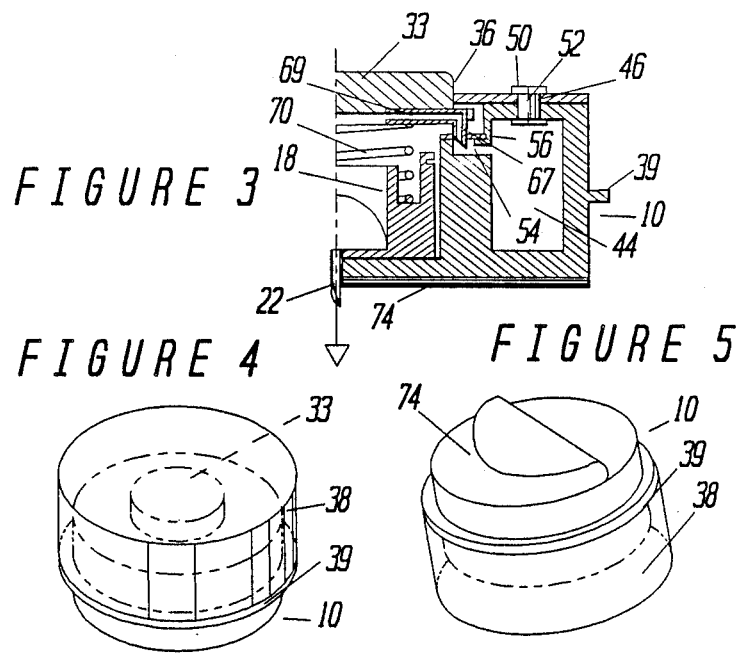
FIGURE 3
FIGURE 4
FIGURE 5
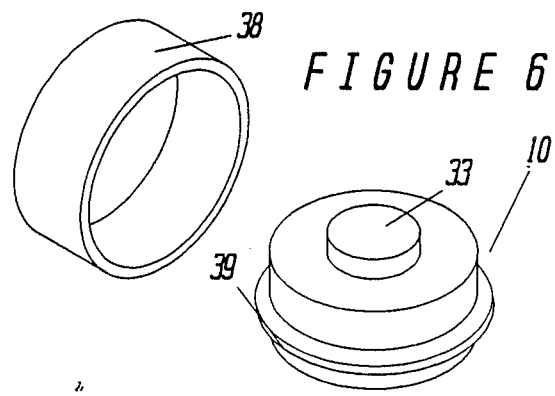
FIGURE 6

4,894,054

PRELOADED AUTOMATIC DISPOSABLE SYRINGE

BACKGROUND OF THE INVENTION

1. Field of the Invention

This invention relates to a hypodermic medicinal injector and, in particular, to a hypodermic syringe which is safe and capable of one time use by patients, handicapped, totally blind or aged persons and children.

2. Brief Statement of the Prior Art

Various devices have been marketed for automated injection of medication. A currently marketed system under the trade name Medi-Jector Easy is promoted as a needle-free, insulin injection system. While this device avoids the use of injection needles, it is intended for use by medically trained personnel to maintain proper sterility, and it is not a disposable injection system that can be readily used by patients, or incapacitated persons.

Another device which has been recently introduced is marketed under the name Inject-Ease. This device uses a hypodermic needle and has interchangeable spacer rings to control the depth of needle penetration.

None of the devices currently marketed provide a disposable needle type syringe for application of medication which is safe, sterile and is adaptable for use by patients, including children and handicapped and elderly patients. In many applications, there is no current substitute for administration of medication by medically trained and skilled persons, since there is no syringe which heretofore has been available with accurately measured dosages of medication, and which can be used by the patient. Thus, diabetic patients, or patients suffering chronic allergies, must be dependent upon receiving medical attention and care for administration of medication.

A syringe for use by patients must be disposable, with a design which will prevent reloading, thereby avoiding misuse of the syringe and the possibility of cross infection with agents such as AIDS viruses. The hypodermic needle of the syringe should be totally protected from contamination, and the syringe should be capable of mass production, thereby insuring its low cost. It is a desirable objective, at this time, to supply the syringe with variable size needles from ⅛ to ¼ inch and of 23 to 30 gauge, for pediatric, adults and obese patients. It is also an objective to provide a syringe which is preloaded by a licensed pharmaceutical company, insuring sterility and accuracy of dosage and strength of the medication.

BRIEF STATEMENT OF THE INVENTION

This invention comprises a pre-charged, disposable syringe capable of use by patients. The syringe includes a housing with a cover having a central aperture which receives an actuator button. The actuator button extends to an internal piston which is mounted over a medication ampoule. The ampoule has a dependent hypodermic needle which is slidably received in the housing for movement between recessed and projected positions. In its recessed position, the ampoule is totally contained and supported within the housing, and in its projected position, the hypodermic needle projects out of the housing. The housing contains an actuator spring, which is compressed and biased to move the piston and the ampoule into its projected position. The medication discharged from the ampoule by the mechanically coupled piston, or by the release of air from an internal air pressure chamber. The actuator button is locked for safety with a detent and plastic ring and is covered with a protective, removable cap to prevent accidental or unintended injection of the medication.

BRIEF DESCRIPTION OF THE DRAWINGS

The invention will be described with reference to the figures of which:

FIG. 3 is a partial, elevational sectional view of the embodiment of FIG. 1 is its discharged state;

FIG. 4 is a perspective view of the assembled and loaded syringe of the invention;

FIG. 5 illustrates removal of the protective tape from the underside of the syringe;

FIG. 6 is a view of the syringe, uncovered, and in a position to inject its medication;

DESCRIPTION OF PREFERRED EMBODIMENTS

Figure 1:
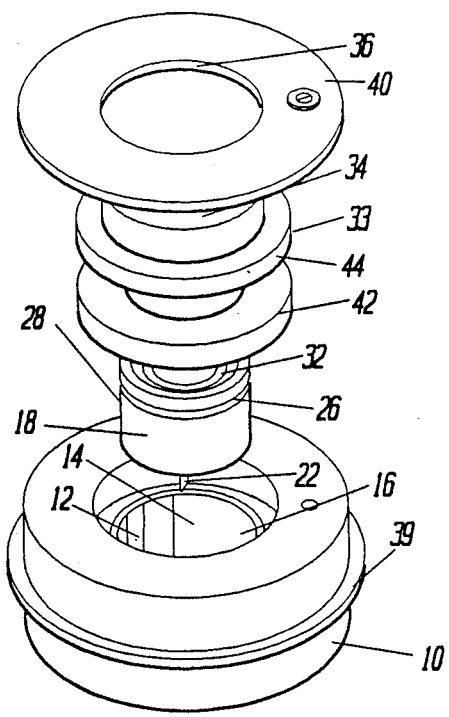
FIG. 1 is an exploded perspective view of the air activated embodiment of the invention.

Referring now to FIG. 1, the invention is illustrated in exploded view. The particular embodiment illustrated in FIG. 1 is the air activated device. The device has a housing 10 which is preferably cylindrical of relatively low height or elevation, and has a central cavity 12 which receives the operating mechanism. The central cavity 12 has an internal well 14 with a right-angle, vertical cylindrical wall 16 which slidably receives a cylindrically shaped ampoule member 18. The ampoule member 18 has a hypodermic needle 22 that extends through its under surface and communicates with the medication chamber, described in greater detail with reference to FIG. 2. An annular groove 26 is provided about the outer side wall 28 of the ampoule 18 which is engaged by a sealing plastic ring (shown in FIG. 2). The upper end of the sidewall of the ampoule 18 has an annular recess 32 which serves as a chamber for housing a compression spring (also shown in FIG. 2). The actuator button 33 has a central upright boss 34 which is received in the central aperture 36 of the cover 40. The button 33 and has a circular base 44 which carries, on its undersurface, a knife 42 having a circular blade.

Figure 2:
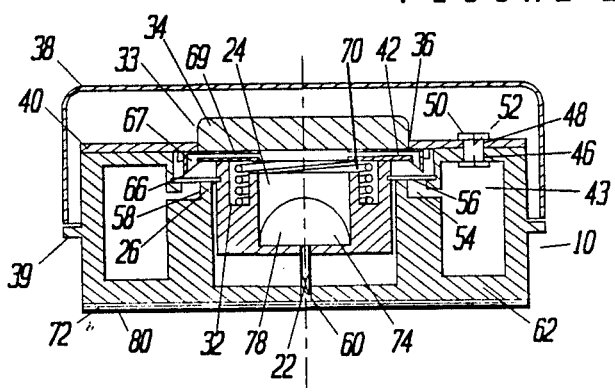
FIG. 2 is an elevational sectional view of the embodiment of FIG. 1, fully loaded in a static, preactivated state.

Referring now to FIG. 2, the invention will be described in greater detail. As shown in FIG. 2, the housing 10 has an outer annular chamber 43 which is the air supply chamber for the mechanism. A fill port 46 is provided in the upper wall of the air chamber and this port 46 communicates with an aligned aperture 48 in the cover. A pneumatic valve 50 is inserted in the aligned aperture 48 and fill port 46. This valve 50 is of a general grommet-shape with a through passage 52 that is normally sealed by the resilient deformation of the valve member under the internal pressure within the air chamber. The internal air chamber communicates with the interior, medication chamber 24 through a valve 54 which is sealed by a plastic ring 56. The valve has an annular seat 58 and is entirely covered by this plastic ring seal 56. The seal 56 is received in annular groove 26 about the ampoule member 18, and thus also serves as a detent to restrain the ampoule member 18 and needle 22 within the housing. Seated within the medication chamber 24 is the cylindrical cup-shaped ampoule member 18 which supports the hypodermic needle 22 on its under surface. The hypodermic needle 22 is aligned with a central through aperture 60 in the bottom wall 62 of the housing 10 and is of sufficient length that when the ampoule member 18 is in its illustrated, retracted position, the hypodermic needle 22 is withdrawn from this aperture 60. The ampoule member 18 has sufficient travel within the housing 10 to project the needle 22 through the aperture 60 and a predetermined distance into the tissue of the patient.

The actuator button 33 has a central raised boss 34 that extends through the central aperture 36 of the cover 40. The button 33 is enclosed within a protective cover 38 which seats against an annular rim 39 about the mid-portion of the housing 10. The cover 38 can be sealed to the housing by a tear tape, if desired. The button 33 supports, on its undersurface, a knife 42 with a circular blade. The knife blade has a sharp circular cutting edge 66 which is aligned with the plastic ring 56 so that it will puncture this plastic ring and permit the discharge of the pressured air from the annular air chamber 43 past the valve and into the ampoule chamber. The knife also has a circular groove 67 which communicates with a passageway 69 that extends into communication with the internal chamber 24 of the ampoule member 18.

The ampoule member 18 has an annular well 32 in its upper edge which provides a chamber for the actuator spring 70. The actuator spring 70 is a compression coil spring biased between the undersurface of the button 33 and the bottom wall of the annular well 32. This spring has sufficient strength and resiliency to advance the ampoule member 18 instantaneously upon release of the detent, previously described, and extend the hypodermic needle 22 through the frangible sterile tape 72 on the undersurface of the housing and into the patient's subcutaneous space. The extended positions of the ampoule member 18 and needle 22 are shown in FIG. 3. This extension of the ampoule member 18 and hypodermic needle 22 occurs sufficiently rapidly to precede the application of air pressure through circular groove 67 in the knife 42 and the passageway 69 of the button. Thus the needle 22 is extended before air pressure is applied to the ampoule 74 contained within the ampoule chamber 24. The ampoule 74 is formed by an elastic balloon which is received within and sealed to the inner walls of the ampoule chamber, containing medication 78 within its sealed interior. The air pressure supplied by the air chamber 43 through the air valve 54 and into the ampoule chamber is sufficient to collapse the medication balloon and inject the medication 78 contained within the balloon into the patient.

The undersurface of the housing 10 has a frangible sterile tape 72 which is permanently bonded to the housing, and which overlies the through aperture 60, and an overlying, protective sterile tape 80. The protective overlay tape 80 is bonded to the housing and the sterile tape 72 with a pressure sensitive adhesive to permit its removal from the injection device immediately prior to use.

Figure 7:
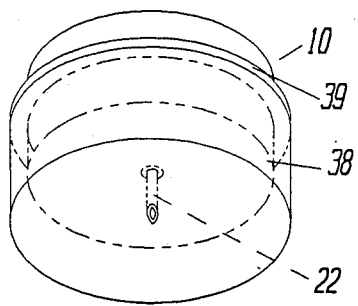
FIG. 7 is a view of the syringe after use, with the cover replaced on its undersurface for disposal.

FIG. 4 illustrates the hypodermic syringe of the invention as it would be received by the patient. The syringe is preloaded with a precisely measured dosage of medication and has the proper selection of needle size for the patient. All of this information can be coded on the syringe itself. The protective cover 38 overlies the actuator button 33, and must be removed by the patient for access to the button. As shown in FIG. 5, the patient or user will first remove the protective overlay tape 80, exposing the underlying frangible, sterile tape. As shown in FIG. 6, the patient will then position the syringe against a suitable skin surface. Preferably, the undersurface of the housing and the sterile tape 72 is coated with an antiseptic pressure sensitive adhesive so that, when placed on the skin of a patient, the undersurface of the device will disinfect and be slightly tacky and will stick to the skin of the patient. The patient then depresses the actuator button 33, breaking the detent of the plastic ring 56. This will release the spring 70 to advance the knife 42 through the plastic ring 56, and permit the ampoule member 18 to be ejected into its extended position. The air pressure which is also released from the annular air chamber 43 will fill the ampoule chamber 24, raising its internal pressure sufficiently to eject the medication from the ampoule 74. Once the injection is completed, the patient removes the device which is disposed as it cannot be readily reloaded for reuse. For this purpose, the protective cover 38, which was removed from over the actuator button, is replaced on the underside of the syringe, totally enclosing the needle 22, as shown in FIG. 7.

Figure 8:
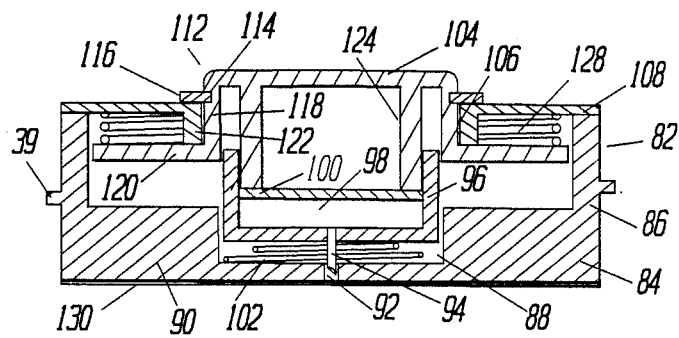
FIG. 8 is an elevational sectional view of a spring activated mechanism, in a static, preactivated state.

Referring now to FIG. 8, the alternative embodiment of the invention will be described. As there illustrated, this device 82 has a cylindrical, cup-shaped housing 84 having an outer wall 86 defined by a right-angle cylindrical wall, and a central lesser diameter well 88. The bottom wall 90 of the housing 84 has a central through aperture 92 which slidably receives the hypodermic needle 94. The ampoule member 96 is a cylindrical cup-shaped member which contains medication 98 and which also receives a slidable piston 100. The piston 100 engages the inside wall of the cylindrical member 96 in a sliding seal which prevents leaking of the medication from the ampoule member 96. The ampoule member 96 is resiliently biased into its retractable position by a helical coil spring 102 which is seated in the central well 88 of the housing and which is collapsed when the ampoule member 96 is driven into its extended position.

The actuator button 104 is slidably received in a central aperture 106 of the top cover 108. The actuator button 104 is restrained to this cover by a detent 112 formed by an annular groove 114 about its outer, upper wall in which is seated a resilient clip washer 116. The button 104 has a cylindrical skirt 118 and a single, outwardly flared flange 120. The cover 108 has a central inwardly and downwardly dependent skirt 122 which receives the cylindrical skirt 118 of the actuator button 104.

A cylindrical boss 124 is downwardly dependent from the undersurface of the button 104 and has a diameter to permit it to be received within the ampoule member 96. The boss 124 is immediately above, and attached to, the piston 100 which is slidably contained within the ampoule member 96. An actuator spring 128 in the form of a compression coil spring is resiliently biased between the undersurface of the cover and the upper surface of the flange of the actuator button. When the device is in its armed and loaded condition as illustrated in FIG. 8, the actuator spring 128 is compressed.

Figure 9:
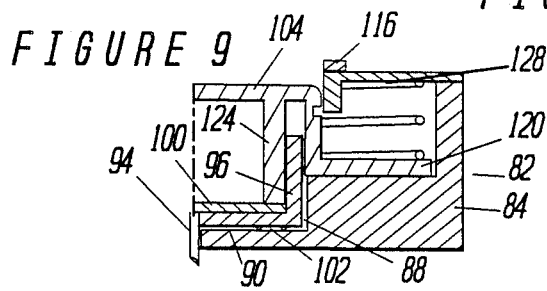
FIG. 9 is an elevational sectional view of the device of FIG. 8 is its discharged state.

In use, the patient removes the protective overlay tape 130 from the undersurface of the device, in the manner previously described and illustrated in FIG. 5. Preferably, the undersurface of the device has an antiseptic, pressure sensitive coating permitting its application to the skin of a patient. In this position, the device is ready for injection of the medication which is contained within the ampoule member 96. The patient presses on the actuator button 104 sufficiently to override the resilient detent of the circular clip washer 116. This permits the actuator spring 128 to be released, forcing the ampoule chamber 96 outwardly into its extended position, which is shown in FIG. 9. In this position, the ampoule needle 94 projects through the skin of the patient. When the ampoule chamber 96 bottoms against the bottom wall 90 of the central well 88, the actuator spring 128 continues the travel of the actuator button, and advances the piston 100 through the ampoule chamber 96, ejecting the medication 98 in this chamber through the hypodermic needle 94, into the patient. The resilient bias of the retraction spring 102 is designed to be less than the force required for slidably advancing the piston 100 in the ampoule chamber 96, thereby ensuring that the medication is not prematurely ejected from the ampoule chamber.

Special Advantages of the Invention

The ejection operation of both embodiments of the invention is smooth and continuous with the initial advance of the ampoule chamber and hypodermic needle which eject with sufficient force for the needle to penetrate the skin of the patient. This initial movement is immediately followed by the continuous injection of the medication contained within the ampoule chamber. Since the device of this invention can not be readily reloaded it is safe for prescription as a disposable, single use medication. The device is very safe for use by patients and since it can only be used once, there is no possibility of passing a contagious or infectious diseases such as AIDS. The device can be provided with variable capacity and with needles of varied sizes and lengths suitable for pediatric use, or use by adults or obese persons.

Since the device can be readily used by the patient, it is ideally suited for diabetic control, for anaphylatic shock, such as encountered with hypersensitive or allergic individuals, e.g., for dispensing of medication for bites by snakes, bees, insects, etc. As the device is entirely pre-loaded, little physical ability and judgement is required of the patient and the device can be used by children, handicapped persons or persons whose judgement or dexterity has been temporarily impaired by shock.

The device can be used to inject only vertically as it has a large exterior surface that is applied to the skin which is relatively large compared to the depth of the needle. Accordingly the device cannot be used for intravenous injections which, of course, require skilled and licensed personnel.

Preferably, the device is provided with a transparent structure, e.g., formed of transparent plastics, thereby readily permitting observation of the contents of the ampoule. The actuator button can be suitably colorcoated, e.g., preferably molded of a red colored plastic. In its preferred embodiment, as shown in FIG. 3, the device also includes a protective cover 132 which is mounted about the side wall 134 of the housing 84 and which engages against an annular rim 136 that extends about the periphery of the housing, preferably at its mid-portion. This permits the cover to be reapplied over the opposite end of the housing after use, thereby encasing the needle in a protective chamber when the device is disposed.

The extreme compactness of the device and its low profile stabilizes the device when used by the patient. Additionally, the low profile and compactness of the injection device greatly aids packaging and distribution by the pharmaceutical supply house.

All of the component parts of the injection device can be fabricated of readily available materials such as plastics using injection molding techniques for mass production. The device can be marketed with significantly lower costs than conventional syringes. The device can be assembled and preloaded with measured amounts of medication under sterile conditions by the pharmaceutical supply house and can be sealed with the frangible sterile tape and the protective overlay tape, isolating the medication from contact with the external environment.

The invention has been described with reference to the illustrated and presently preferred embodiment. It is not intended that the invention be unduly limited by this disclosure of the presently preferred embodiment. Instead, it is intended that the invention be defined, by the means, and their obvious equivalents, set forth in the following claims:

What is claimed is:

1. A disposable, subcutaneous injection syringe which comprises:
   a. a cylindrical housing having an outer diameter greater than its length and having a central, cylindrical well, a first aperture in its bottom wall and a second aperture in its top wall;
   b. a cylinder having an outer diameter to be received in said cylindrical well of said housing and received therein for sliding movement between said apertures, a through bore in the bottom wall of said cylinder and a hypodermic needle permanently mounted therein, and a piston slidably received in said cylinder;
   c. a dispenser carriage mounted in said housing and moveable therein through an axial distance less than said outer diameter of said cylinder, between retracted and extended positions;
   d. a trigger button carried on said carriage and projecting through said second aperture;
   e. means coupling said piston to said carriage;
   f. cylinder retraction means within said housing to maintain said needle withdrawn in said housing;
   g. a single actuator spring received within said housing and bearing against said cylinder to extend said needle through said first aperture in the bottom wall of said housing;
   h. a single detent, which engages said carriage in its retracted position and restrains its movement in said housing; and
   i. a sterile seal cover extending across said first aperture.

2. The syringe of claim 1 wherein said detent includes an annular groove about said actuator button and a snap ring engaged in said annular groove and bearing against the top wall of said housing.

3. The syringe of claim 2 wherein said carriage includes an annular flange within said housing and wherein said actuator spring is biased between the inside top wall of said housing and said annular flange.

4. The syringe of claim 3 wherein said carriage bears, on its undersurface, a boss which is received within said cylinder and which abuts against said piston.

5. The syringe of claim 4 including a medication within said cylinder.

6. The syringe of claim 1 including a protective sheet material overlying said seal cover and bonded thereto by a peelable, pressure sensitive adhesive.

7. The syringe of claim 6 wherein said pressure sensitive adhesive includes an antiseptic agent.

8. The syringe of claim 6 wherein said pressure sensitive adhesive includes a tacifier agent, rendering the underside of said syringe tacky upon removal of said protective sheet material.

9. The syringe of claim 1 wherein said cylinder retraction means is a helical coil spring which is received between the bottom wall of said cylinder and the bottom wall of said housing.

10. The syringe of claim 1 including a cup-shaped cap having an inside diameter slightly greater than the outside diameter of said housing and received over an end of said housing, and wherein said housing is of the same outside diameter at each of its ends, whereby said cap can be placed over the top wall end of said housing prior to use of said syringe, and can be reversed and placed over the bottom wall end of said housing after use of said syringe.

11. The syringe of claim 10 wherein said housing has an annular rim about its mid-portion and said cap seats against said annular rim.

12. The syringe of claim 1 including a protective sheet material overlying said seal cover and bonded thereto by a peelable, pressure sensitive adhesive.

13. The syringe of claim 1 wherein said pressure sensitive adhesive includes an antiseptic agent.

14. The syringe of claim 12 wherein said pressure sensitive adhesive includes a tacifier agent, rendering the underside of said syringe tacky upon removal of said protective sheet material.

15. The syringe of claim 1 wherein said cylinder retraction means is a helical coil spring which is received between the bottom wall of said cylinder and the bottom wall of said housing.

16. A disposable, subcutaneous injection syringe which comprises:
   a. a housing having a first aperture in its bottom wall and a second aperture in its top wall;
   b. a cylinder received in said housing mounted in said housing for sliding movement between said apertures, a through bore in the bottom wall of said cylinder and a hypodermic needle permanently mounted therein, and a piston slidably received in said cylinder;
   c. a dispenser carriage mounted in said housing and moveable therein between retracted and extended positions;
   d. a trigger button carried on said carriage and projecting through said second aperture;
   e. means coupling said piston to said carriage;
   f. cylinder retraction means within said housing to maintain said needle withdrawn in said housing;
   g. an actuator spring received within said housing and bearing against said cylinder to extend said needle through said first aperture in the bottom wall of said housing;
   h. a detent engaging said carriage in its retracted position and restraining its movement in said housing;
   i. a sterile seal cover extending across said first aperture; and
   j. an annular chamber within said housing, and an internal passageway communicating between said annular chamber and said cylinder, above said piston.

17. The syringe of claim 16 wherein said annular chamber has an external port sealed with a check valve to permit air pressurization of said annular chamber and wherein said internal passageway includes frangible valve means.

18. The syringe of claim 17 wherein said internal passageway includes an annulus surrounding said cylinder, and said frangible valve means is an annular ring seated in said annulus.

19. The syringe of claim 18 wherein said cylinder has an annular groove about its outer wall and said annular ring is seated therein to also function as said detent to restrain movement of said cylinder in said housing.

20. The syringe of claim 19 including a knife carried on the underside of said actuator button immediately above said frangible annular ring.

21. The syringe of claim 16 including a cup-shaped cap having an inside diameter slightly greater than the outside diameter of said housing and received over an end of said housing, and wherein said housing is of the same outside diameter at each of its ends, whereby said cap can be placed over the top wall end of said housing prior to use of said syringe, and can be reversed and placed over the bottom wall end of said housing after use of said syringe.

22. The syringe of claim 21 wherein said housing has an annular rim about its mid-portion and said cap seats against said annular rim.

* * * * *